United States Patent
Martin et al.

[11] Patent Number: 5,142,077
[45] Date of Patent: Aug. 25, 1992

[54] ALUMINUM MAGNESIUM HYDROXY COMPOUNDS

[75] Inventors: Roland Martin, Weinheim; Klaus Schanz, Da-Schauernheim; Bruno Kaufmann, Frankenthal, all of Fed. Rep. of Germany

[73] Assignee: Giulini Chemie GmbH, Ludwigshafen/Rh., Fed. Rep. of Germany

[21] Appl. No.: 248,950

[22] Filed: Sep. 23, 1988

[30] Foreign Application Priority Data

Sep. 23, 1987 [DE] Fed. Rep. of Germany ....... 3731919

[51] Int. Cl.$^5$ .......................... C07F 5/06; B01J 23/02; B01J 23/06; C01F 7/02
[52] U.S. Cl. ..................................... 554/76; 423/115; 423/600; 502/341; 556/179; 556/170
[58] Field of Search ............... 423/115, 122, 593, 596, 423/600; 501/118, 119, 121; 502/341; 556/170, 179

[56] References Cited

U.S. PATENT DOCUMENTS

| | | | |
|---|---|---|---|
| 3,907,715 | 9/1975 | Arai et al. | 423/600 |
| 3,980,685 | 9/1976 | Miyata et al. | 548/402 |
| 4,392,979 | 7/1983 | Lee et al. | 423/600 |
| 4,412,018 | 10/1983 | Finlayson et al. | 523/508 |
| 4,434,075 | 2/1984 | Mardis et al. | 252/315.2 |
| 4,434,076 | 2/1984 | Mardis et al. | 252/315.2 |
| 4,539,195 | 9/1985 | Schanz et al. | 423/430 |
| 4,639,362 | 1/1987 | Schanz | 423/554 |
| 4,724,098 | 2/1988 | Kalz et al. | 252/315.2 |

FOREIGN PATENT DOCUMENTS

| | | |
|---|---|---|
| 204240 | 12/1986 | European Pat. Off. |
| 2061156 | 7/1971 | Fed. Rep. of Germany |
| 50-69525 | 5/1980 | Japan |

*Primary Examiner*—Gary P. Straub
*Assistant Examiner*—Ngoc-Yen Nguyen
*Attorney, Agent, or Firm*—Spencer, Frank & Schneider

[57] ABSTRACT

Aluminum magnesium hydroxy compounds of the formula $$Al_xMg_y(OH)_{35-z}R_z \cdot nH_2O$$

in which R represents an anion of at least one monocarboxylic acid having from 2 to 22 carbon atoms, and n, x, y and z are defined by:

$0 \leq n \leq 10$ $3 \leq x \leq 9$ $4 \leq y \leq 13$ $3 \leq z \leq 5$ and $3x + 2y = 35$ are described.

14 Claims, 4 Drawing Sheets

ALUMINUM MAGNESIUM HYDROXY COMPOUNDS

CROSS REFERENCE TO RELATED APPLICATION

This application is related to our concurrently filed application entitled "Gel Compositions Useful for Cosmetics" U.S. application Ser. No. 07/249,304 the disclosure of which is incorporated herein by reference.

1. Field of the Invention

The present invention relates to thickening, thixotropy imparting, stabilizing and anti-settling agents, for example for dyes, lacquers, paints, putties, waxes, adhesives and cosmetics, based on aluminum magnesium hydroxy compounds and to a process of manufacturing them.

2. Technology Review

In the above-mentioned fields, organophilic laminar silicates, such as organophilic montmorillonites, hectorites and bentonites, have been employed for some time as thickening and thixotropy imparting agents. These agents are produced when swellable laminar silicates are covered with polar, long-chain, organic molecules, usually quaternary ammonium compounds. The resulting organophilic laminar silicates are described in numerous patents. For example, U.S. Pat. No. 4,724,098 discloses organophilic laminar silicates whose exchangeable cations are wholly or partly replaced by quaternary ammonium compounds. These laminar silicates can be dispersed in an organic solvent to form a gel. If natural argillaceous minerals are employed as the laminar silicates, the raw product must first be cleaned by removing the non-swellable material. Moreover, since the laminar silicate should be present in a highly swellable form, it is further recommended to produce this form, for example, the sodium form, by ion exchange. Organophilic, modified, swellable, laminar silicates containing quaternary ammonium compounds and their uses as thickening agents are disclosed in U.S. Pat. No. 4,434,076.

U.S. Pat. No. 4,434,075 and U.S. Pat. No. 4,412,018 disclose gel-forming, organophilic clays. As in the previously described organophilic laminar silicates, the exchangeable cations of these clays are replaced with complex cations, for example, quaternary ammonium, phosphonium or sulfonium ions. However, these clays may also contain other cation complexes and anion complexes. The complexes are formed during the reaction of the aqueous clay slurry with an organic anionic or an organic cationic compound.

The organophilic silicate complexes of U.S. Pat. Nos. 4,434,075 and 4,412,018 are dispersible in organic liquids also forming a gel. Depending on their composition, such gels are claimed to be suitable, among other things, for lubricating greases, oil-based slurries, binders for molding sand, adhesives and sealants.

However, it has now been found that many of the organophilic clays do not meet the demands placed upon them. For example, depending on the quality of the starting clay, discolorations may occur in the basic pastes. These pastes consist of an organic solvent having a solids content of about 10%. Such discolorations may be disadvantageous in many applications and prevent the manufacture of transparent or truly white products. Moreover, the dispersion stability of many organophilic laminar silicates in organic solvents is unsatisfactory. This results in separation of solvent after only a short period of time and formation of a hard sediment at the bottom of the container during storage of the basic pastes.

The color of the modified bentonites, which varies from light yellow to brown, is a major problem encountered in the incorporation of organically modified bentonites into cosmetic formulations. This inherent coloration results if the organically modified bentonites are dispersed in various organic solvents, such as toluene, cyclohexane, silicone oil or paraffin oil.

Moreover, cosmetic preparations in which organically modified bentonites are contained as thickening or thixotropy imparting agents may also produce skin irritations. This is caused primarily by the quaternary ammonium compounds which are employed for the organic modification of the bentonites and are contained therein to between 30 to 50 weight percent.

SUMMARY OF THE INVENTION

It is thus an object of the present invention to find compounds which do not have the drawbacks of the above organophilic laminar silicates.

Surprisingly, this can be accomplished with compounds of the formula

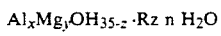

$$Al_xMg_yOH_{35-z} \cdot Rz \; n \; H_2O$$

where R represents the anion of a monocarboxylic acid having 2 to 22 carbon atoms and the indices x, y and z meet the following conditions:

$$3 \leq x \leq 9$$
$$4 \leq y \leq 13$$
$$3 \leq z \leq 5$$
$$3x + 2y = 35.$$

M is a number in the range 0 to 10.

DETAILED DESCRIPTION OF THE INVENTION

The novel compounds having the above formula are produced by reacting, with stirring and at temperatures between about 20° C. and 100° C., preferably between about 20° C. and 60° C., an aqueous suspension of a compound of the formula $Al_xMg_y(OH)_{35-z}(SO_4)_{z/2} \cdot n\text{-}H_2O$ (in which x, y and z have the above-stated definitions), with the aqueous suspension of an alkali salt of a monocarboxylic acid containing 2 to 22 carbon atoms. Preferably the reaction is performed with shear forces acting on the aqueous suspensions. Under such process conditions, the reaction is complete within 2 hours in many cases.

The reaction product can be separated from the aqueous suspension by known processes, and preferably by filtration. The filter cake is washed with water to remove the adhering alkali sulfate until no $SO_4^{2-}$ can be found by barium chloride in the wash water. The filter cake is then dried at temperatures between about 60° C.

and 130° C., and preferably at about 80° C. to 110° C., for example in a shelf dryer. Other types of drying devices can also be used.

In another drying variation, the filter cake, once it is free of sulfate, is resuspended in water and is spray-dried, with the entrance temperature $T_E$=about 250° C. to 350° C., preferably about 270° C. to 300° C., and the exit temperature TA =about 80° C. to 130° C., preferably about 90° C. to 110° C.

According to other variations of the process, the alkali salt of a monocarboxylic acid is added in solid form to the aqueous suspension of the compound $Al_x Mg_y(OH)_{35-z}(SO_4)_{z/2} \cdot nH_2O$, with all other process features remaining the same.

The Al-Mg compounds employed as starting materials in the process of the invention are known in the art. For example, they are disclosed in U.S. Pat. No. 4,639,362, entitled "Process for the Production of Magaldrate" of the formula $Al_5Mg_{10}(OH)_{31}(SO_4)_2 \cdot x\ H_2O$. Monocarboxylic acids are commercially available compounds. Industrial grade mixtures of monocarboxylic acids may be used. The alkali salts can be produced as indicated in the examples.

Figure 1:
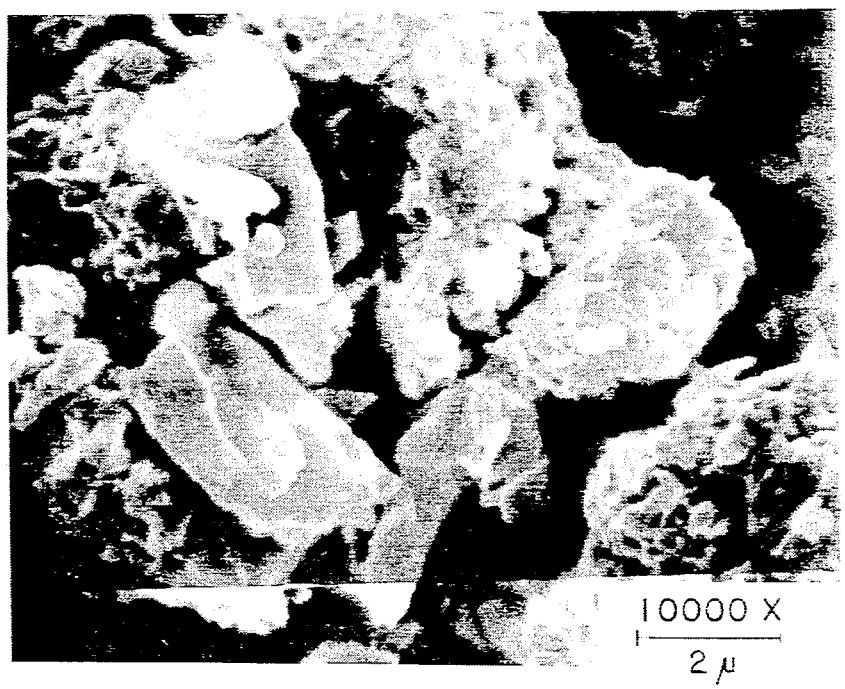
FIG. 1 is a scanning electron micrograph showing the laminar structure of the product of Example 10 set forth below.

The Al-Mg compounds are solid, white and odorless, crystalline substances. Their structure is characterized with the aid of X-ray diffraction and scanning electron microscopy. X-ray diffraction patterns show that the compounds are crystalline. The layer or laminar structure is evident from scanning electron micrographs (see FIG. 1).

In comparison with commercially available organically modified hectorite or sodium bentonite, the compounds of the invention are noticeably whiter. The degree of whiteness is a measure of the color of the substances and was determined by means of a Tricolor LFM 3 color measuring device (manufactured by Dr. Lange) against an enamel white standard. Table 1 shows the whiteness of the products from Examples 6 to 17 below and the whiteness of two commercially available products. This table clearly shows that the compounds of the invention have a noticeably higher degree of whiteness than the commercially available products.

TABLE 1

| Comparison of Whiteness | |
| --- | --- |
| Product of Example 6: | 98.1 |
| Product of Example 7: | 98.0 |
| Product of Example 8: | 98.1 |
| Product of Example 9: | 98.2 |
| Product of Example 10 | 97.9 |
| Product of Example 11: | 98.4 |
| Product of Example 12: | 98.3 |
| Product of Example 13: | 98.2 |
| Product of Example 14: | 98.1 |
| Product of Example 15: | 98.3 |
| Product of Example 16: | 98.4 |
| Product of Example 17: | 98.1 |
| Sodium bentonite | 91.3 |
| Organically modified hectorite | 91.8 |

The experiments described below show the efficiency of the products of the invention as an anti-settling agent in a concentration of 2% by weight.

Formulations were produced as described in Table 2 and the "settling curve" was determined by way of turbidity measurements made with the air of an Eppendorf photometer.

In a 300 ml beaker, the optical extinction of the paraffin oil solvent was set at 0 (100% transmissibility). The same beaker was used for each test. All samples were tested at a 2% by weight concentration in paraffin oil. They were homogeneously suspended by stirring and were then stirred for 3 minutes at 100 rpm. The stirrer was turned off and the decrease of extinction monitored on a graph. The transmissibility value obtained immediately after stopping the stirrer was set to 0%.

Table 2 clearly shows that the products of the present invention settle much less easily than the comparison products. This is an advantage when using the products, for instance, in connection with pigments and less soluble dyes.

TABLE 2

| | Settling Tests (% Transmissibility) | | | | |
| --- | --- | --- | --- | --- | --- |
| Product of Example | 1 h | 2 h | 3 h | 6 h | 8 h |
| 6 | 0.2 | 0.4 | 1.0 | 11.9 | 21.0 |
| 7 | 0.8 | 1.2 | 1.4 | 4.7 | 9.0 |
| 8 | 1.0 | 2.0 | 2.8 | 13.6 | 23.5 |
| 9 | 0.8 | 0.8 | 1.2 | 4.7 | 8.5 |
| 10 | 0.8 | 0.8 | 0.8 | 3.5 | 7.0 |
| 11 | 0.8 | 0.8 | 1.2 | 2.5 | 5.8 |
| 12 | 0.4 | 0.4 | 0.4 | 1.6 | 5.5 |
| 13 | 0.2 | 0.2 | 0.2 | 1.5 | 5.3 |
| 14 | 0.2 | 0.2 | 0.2 | 1.5 | 5.0 |
| 15 | 0.2 | 0.2 | 0.2 | 1.6 | 5.4 |
| 16 | 0.4 | 0.6 | 0.8 | 2.0 | 6.1 |
| 17 | 0.6 | 0.6 | 1.0 | 2.5 | 6.3 |
| Na-bentonite | 2.3 | 7.6 | 12.5 | 33.0 | 51.0 |
| organically modified hectorite | 2.0 | 6.5 | 9.0 | 22.2 | 33.0 |

Separately from the above determination, the "settling volume" was determined as a function of time in a 100 ml measuring cylinder. For this purpose, the preparation was shaken 20 times vertically and 20 times horizontally and was then allowed to settle. The settling volume provides information about the easy dispersibility of the organic products of the present invention in a particular solvent under the influence of low shear forces.

In contrast to the settling tests reflected in Table 2, the products in Tables 3 and 4 were suspended (in a 2% by weight concentration) in the respective solvent together with a substance which is not soluble in this solvent (e.g. aluminum chlorhydrate having a grain size of 90% in a range between 10 μm and 75 μm) in a 15% concentration. It can be seen that the suspended products settle less easily if the substances from Examples 6 to 11 are added.

TABLE 3

| | Settling volume (ml) in Silicone Oil (Type 345 - Dow Corning) | | | | | | | | | |
| --- | --- | --- | --- | --- | --- | --- | --- | --- | --- | --- |
| Product from | 0.5 min | 1 min | 3 min | 7 min | 10 min | 20 min | 30 min | 60 min | 2 h | 14 h |
| Example 6 | 99 | 98 | 98 | 91 | 90 | 80 | 75 | 65 | 53 | 23 |
| Example 7 | 100 | 100 | 99 | 98 | 97 | 93 | 89 | 74 | 58 | 24 |
| Example 8 | 100 | 100 | 98 | 96 | 95 | 90 | 85 | 72 | 56 | 24 |
| Example 9 | 100 | 99 | 98 | 96 | 94 | 88 | 82 | 77 | 61 | 27 |

TABLE 3-continued

| | Settling volume (ml) in Silicone Oil (Type 345 - Dow Corning) | | | | | | | | |
|---|---|---|---|---|---|---|---|---|---|
| Product from | 0.5 min | 1 min | 3 min | 7 min | 10 min | 20 min | 30 min | 60 min | 2 h | 14 h |
| Example 10 | 100 | 99 | 98 | 96 | 94 | 89 | 81 | 70 | 54 | 27 |
| Example 11 | 100 | 99 | 97 | 94 | 92 | 84 | 78 | 67 | 54 | 25 |
| w/out additive | 98 | 95 | 73 | 44 | 40 | 35 | 32 | 30 | 25 | 25 |
| Na-bentonite | 100 | 99 | 97 | 82 | 68 | 47 | 43 | 38 | 35 | 25 |
| org. modified hectorite | 100 | 99 | 97 | 92 | 91 | 82 | 72 | 62 | 50 | 27 |

TABLE 4

| | Settling Volume (ml) in Paraffin Oil Type Pioneer 2660, highly viscous)-Hansen + Rosenthal | | | | | | | | |
|---|---|---|---|---|---|---|---|---|---|
| Product from | 10 min | 30 min | 1 h | 2 h | 3 h | 4 h | 8 h | 18 h | 24 h |
| Example 6 | 100 | 98 | 97 | 91 | 87 | 82 | 59 | 45 | 43 |
| Example 7 | 100 | 99 | 98 | 96 | 94 | 93 | 77 | 47 | 43 |
| Example 8 | 100 | 99 | 98 | 94 | 92 | 89 | 71 | 48 | 43 |
| Example 9 | 100 | 99 | 97 | 94 | 91 | 89 | 72 | 44 | 43 |
| Example 10 | 100 | 99 | 98 | 94 | 92 | 90 | 73 | 45 | 43 |
| Example 11 | 100 | 98 | 98 | 93 | 91 | 88 | 67 | 45 | 43 |
| Na-bentonite | 100 | 96 | 87 | 61 | 53 | 49 | 44 | 43 | 43 |
| org. modified hectorite | 99 | 98 | 97 | 91 | 85 | 80 | 58 | 45 | 43 |
| without additive | 97 | 94 | 84 | 60 | 50 | 47 | 41 | 40 | 40 |

The invention will now be described in greater detail by way of the following examples which are intended only to illustrate specific embodiments of the invention, and not to limit it. Unless otherwise stated, all parts and percentages are by weight.

EXAMPLE 1: PRODUCTION OF $Al_xMg_y(OH)_{35-z}(SO_4)_{z/2} \cdot nH_2O$

In an open basin 743 g aluminum hydroxide paste containing 42.73% $Al_2O_3$ was diluted with 8995 g water and then 2924.8 g aluminum sulfate solution containing 21.54% $SO_4$ and 4.21% Al were stirred in. The suspension was allowed to stand overnight to permit any $CO_2$ to escape. Then, 1336.7 g MgO containing 60.3% Mg were added under stirring, causing slight heating. Stirring continued for 2 hours and then the suspension was ready for further processing.

Analysis: 2.46% Al; 4.47% Mg, 3.5% $SO_4$.

EXAMPLE 2: PRODUCTION OF SODIUM CAPRYLATE - $C_7H_{15}COO$ Na 800 g caprylic acid was suspended in 7 L water and heated under stirring to 80° C. Then, a solution of 221.8 g NaOH in 500 g water was slowly added and the mixture was cooled to room temperature. The aqueous solution was slowly evaporated and the residue was dried at 105° C. in a drying cabinet. Yield: 877 g (95% theoretical) of a white powder.

EXAMPLE 3: PRODUCTION OF SODIUM MYRISTATE - $C_{13}H_{27}COO$ Na 800 g myristic acid was suspended in 3 L water and the suspension was heated under stirring to 80° C. Then, a solution of 140.2 g NaOH in 350 ml water was slowly added and the mixture permitted to cool to room temperature. This precipitated the sodium myristate and it was filtered using a suction filter. The product was dried carefully in a drying cabinet until a constant weight was obtained.

Yield: 820 g (89% theoretical) of a white powder.

EXAMPLE 4: PRODUCTION OF SODIUM PALMITATE - $C_{15}H_{31}COO$ Na 800 g palmitic acid was suspended in 9 L water and heated under stirring to 80° C. Then a solution of 124.8 g NaOH in 350 ml water was added and the mixture was permitted to cool to room temperature. The residue was filtered out and dried at 105° C. in a drying cabinet.

Yield: 814 g (94% theoretical) of a white powder.

EXAMPLE 5: PRODUCTION OF SODIUM BEHENATE - $C_{21}H_{43}COO$ Na 700 g behenic acid was suspended in 9000 ml water and heated to 80° C. Then a solution of 83 g NaOH in 350 ml distilled water was added. This immediately precipitated the sodium behenate. The suspension was permitted to cool to room temperature and the precipitate was filtered using a suction filter. It was rinsed three times in 200 ml each and the residue dried at 65° C. in a drying cabinet.

Yield: 708 g (95% theoretical) of a white powder.

EXAMPLE 6: PRODUCTION OF $Al_5Mg_{10}(OH)_{31}(CH_3COO)_4$ 119.6 g sodium acetate was suspended with stirring in 1076 g water and was then added to 2000 g of an Al-Mg-hydroxy sulfate suspension produced as in Example 1. The mixture was heated to 80° C. for three hours to complete the reaction, then the suspension was permitted to cool and the insoluble Al-Mg-hydroxy acetate was filtered out. The filtrate was rinsed in water until no further sulfate could be detected. The filter cake was then dried at 105° C. in a drying cabinet until a constant weight was attained.

Yield: 395 g (95% theoretical).

Description: white, odorless, crystalline powder.

Analysis: 11.5% Al in dry state (theory: 11.8%); 20.9% Mg in dry state (theory: 21.3%); 8.3% C in dry state (theory: 8.4%).

| X-ray Powder Pattern (Apparatus: Philipps Automated X-Ray Powder Diffractometer, System APD 15) for Example 6 | | |
|---|---|---|
| Peak No. | 2 - theta | d (pm) | $I/I_o$ |
| 1 | 19.870 | 4 46.45 | 82 |
| 2 | 34.170 | 2 62.18 | 56 |
| | 34.484 | 2 59.86 | 74 |
| | 35.669 | 2 55.07 | 100 |
| | 35.669 | 2 51.50 | 77 |
| 3 | 41.400 | 2 17.00 | |
| 4 | 42.500 | 2 13.00 | |
| 5 | 48.200 | 1 89.00 | |
| 6 | 60.309 | 1 53.34 | 49 |
| | 60.526 | 1 52.84 | 66 |
| | 61.199 | 1 51.32 | 76 |
| | 61.633 | 1 50.35 | 60 |
| | 61.965 | 1 49.63 | 58 |

EXAMPLE 7: PRODUCTION OF Al-MgO-HYDROXY CAPRYLATE Al$_5$Mg$_{10}$(OH)$_{31}$(C$_7$H$_{15}$COO)$_4$ 242.3 g sodium caprylate (from Example 2) was suspended in 2181 g water with stirring and was added to 2000 g Al-Mg-hydroxy sulfate suspension produced as in Example 1. The suspension was heated to 60° C. for one hour to complete the reaction, was permitted to cool and then the insoluble Al-Mg-hydroxy caprylate was filtered off. The filtrate was rinsed with water until no further sulfate could be detected. The filter cake was then dried at 105° C. in a drying cabinet until a constant weight was attained.

Yield: 517 g (96% theoretical).

Description: white, odorless, crystalline powder

Analysis: 9.0% Al in dry state (theory: 9.1%); 16.2% Mg in dry state (theory: 16.4%); 25.0% C in dry state (theory: 26.0%).

X-ray Powder Pattern (Apparatus: Philipps Automated X-Ray Powder Diffractometer. System APD 15) for Example 7

| Peak No. | 2 - theta | d (pm) | I/I$_o$ |
|---|---|---|---|
| 1 | 19.370 | 4 57.84 | 66 |
| 2 | 33.974 | 2 63.65 | 42 |
|   | 34.267 | 2 61.46 | 72 |
|   | 34.506 | 2 59.70 | 88 |
|   | 34.871 | 2 57.07 | 100 |
|   | 35.075 | 2 55.62 | 83 |
|   | 35.608 | 2 51.91 | 62 |
| 3 | 41.4 | 2 17. |   |
| 4 | 42.5 | 2 13. |   |
| 5 | 48.3 | 1 89. |   |
| 6 | 60.652 | 1 525.5 | 67 |
|   | 60.892 | 1 520.1 | 72 |
|   | 61.279 | 1 511.4 | 56 |
|   | 61.714 | 1 501.8 | 46 |

EXAMPLE 8: PRODUCTION OF Al-Mg-HYDROXY MYRISTATE Al$_5$Mg$_{10}$(OH)$_{31}$(C$_{13}$H$_{27}$COO)$_4$ 182.5 g sodium myristate (from Example 3) was suspended in water by stirring and was added to 1000 g of a Al-Mg-hydroxy sulfate suspension produced as in Example 1. The suspension was heated to 60° C. for one hour to complete the reaction, was permitted to cool and the insoluble Al-Mg-hydroxy myristate was then filtered off. The filtrate was rinsed with water until no further sulfate could be detected. The filter cake was then dried at 105° C. in a drying cabinet until a constant weight was attained.

Yield: 321 g (97% theoretical).

Description: white, odorless, crystalline powder

Analysis: 7.3% Al in dry state (theory: 7.4 %); 13.2% Mg in dry state (theory: 13.4 %); 36.3% C in dry state (theory: 37.0%).

X-ray Powder Pattern (Apparatus: Philipps Automated X-Ray Powder Diffractometer, System APD 15) for Example 8

| Peak No. | 2 - theta | d (pm) | I/I$_o$ |
|---|---|---|---|
| 1 | 20.909 | 4 24.48 | 100 |
|   | 21.340 | 4 16.00 | 91 |
|   | 21.560 | 4 11.82 | 72 |
| 2 | 33.916 | 2 64.08 | 35 |
|   | 34.089 | 2 62.78 | 49 |
|   | 34.471 | 2 59.95 | 70 |
|   | 35.069 | 2 55.66 | 68 |

-continued

X-ray Powder Pattern (Apparatus: Philipps Automated X-Ray Powder Diffractometer. System APD 15) for Example 8

| Peak No. | 2 - theta | d (pm) | I/I$_o$ |
|---|---|---|---|
|   | 35.524 | 2 52.49 | 51 |
| 3 | 41.4 | 217. |   |
| 4 | 42.5 | 213. |   |
| 5 | 48.2 | 189. |   |
| 6 | 60.318 | 1 53.31 | 28 |
|   | 60.534 | 1 52.82 | 47 |
|   | 61.649 | 1 50.32 | 42 |

EXAMPLE 9: PRODUCTION OF Al-Mg-HYDROXY PALMITATE Al$_5$Mg$_{10}$(OH)$_{31}$(C$_{15}$H$_{31}$COO)$_4$ 405.9 g sodium palmitate (from Example 4) was suspended by stirring in 3653 g water and was added to 2000 g Al-Mg-hydroxy sulfate suspension produced as in Example 1. The suspension was heated to 60° C. for one hour to complete the reaction, was permitted to cool and then the insoluble Al-Mg-hydroxy palmitate was filtered off. The filtrate was rinsed with water until no further sulfate could be detected. The filter cake was then dried at 105° C. in a drying cabinet until a constant weight was attained.

Yield: 660 g (94% theoretical).

Description: white, odorless, crystalline powder

Analysis: 6.8% Al in dry state (theory: 7.0%); 12.4% Mg in dry state (theory: 12.6%); 39.4% C in dry state (theory: 39.9%).

X-ray Powder Pattern (Apparatus: Philipps Automated X-Ray Powder Diffractometer. System APD 15) for Example 9

| Peak No. | 2 - theta | d (pm) | I/I$_o$ |
|---|---|---|---|
| 1 | 19.702 | 4 50.21 | 59 |
|   | 21.323 | 4 16.35 | 100 |
| 2 | 31.792 | 2 81.23 | 30 |
| 3 | 34.305 | 2 61.17 | 48 |
|   | 34.615 | 2 58.91 | 76 |
|   | 35.169 | 2 54.95 | 64 |
| 4 | 41.4 | 2 17. |   |
| 5 | 42.5 | 2 13. |   |
| 6 | 48.3 | 1 89. |   |
| 7 | 60.700 | 1 52.44 | 49 |
|   | 61.138 | 1 51.45 | 32 |

EXAMPLE 10: PRODUCTION OF Al-Mg-HYDROXY STEARATE Al$_5$Mg$_{10}$(OH)$_{31}$(C$_{17}$H$_{35}$COO)$_4$ 446.8 g sodium stearate was suspended by stirring in 4021 g water and was added to 2000 g Al-Mg-hydroxy sulfate suspension produced as in Example 1. The suspension was heated to 60° C. for one hour to complete the reaction, was permitted to cool and then the insoluble Al-Mg-hydroxy stearate was filtered off. The filtrate was rinsed until no further sulfate could be detected. The filter cake was then dried in a drying cabinet at 105° C. in a drying cabinet until a constant weight was attained.

Yield: 738 g (98% theoretical).

Description: white, odorless, crystalline powder.

Analysis: 6.5% Al in dry state (theory: 6.6%); 11.7% Mg in dry state (theory: 11.9%); 42.2% C in dry state (theory: 42.4%)

Figure 2:
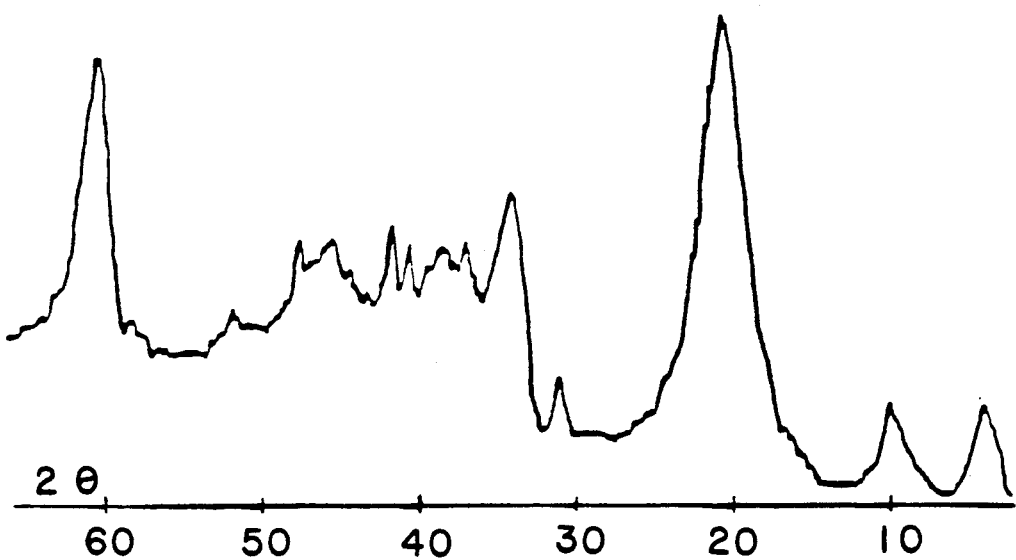
FIG. 2 is the peak pattern for Example 10.

See FIG. 2 for peak pattern for Example 10.

X-ray Powder Pattern (Apparatus: Philipps Automated X-Ray Powder Diffractometer, System APD 15) for Example 10

| Peak No. | 2 - theta | d (pm) | $I/I_o$ |
|---|---|---|---|
| 1 | 19.576 | 4 53.07 | 59 |
|   | 20.794 | 4 26.81 | 91 |
|   | 21.466 | 4 13.59 | 100 |
| 2 | 31.641 | 2 82.53 | 34 |
| 3 | 34.894 | 2 64.25 | 41 |
|   | 34.072 | 2 62.91 | 36 |
|   | 34.401 | 2 60.47 | 47 |
|   | 34.697 | 2 58.32 | 61 |
|   | 35.265 | 2 54.29 | 46 |
|   | 35.5114 | 2 52.56 | 44 |
|   | 35.693 | 1 51.33 | 39 |
|   | 35.873 | 2 50.11 | 34 |
| 4 | 41.4 | 2 17. |  |
| 5 | 42.5 | 2 13. |  |
| 6 | 48.163 | 1 88.77 | 30 |
| 7 | 60.399 | 1 53.13 | 26 |
|   | 60.765 | 1 52.29 | 37 |
|   | 60.974 | 1 51.82 | 35 |
|   | 61.306 | 1 51.08 | 35 |

Figure 3:
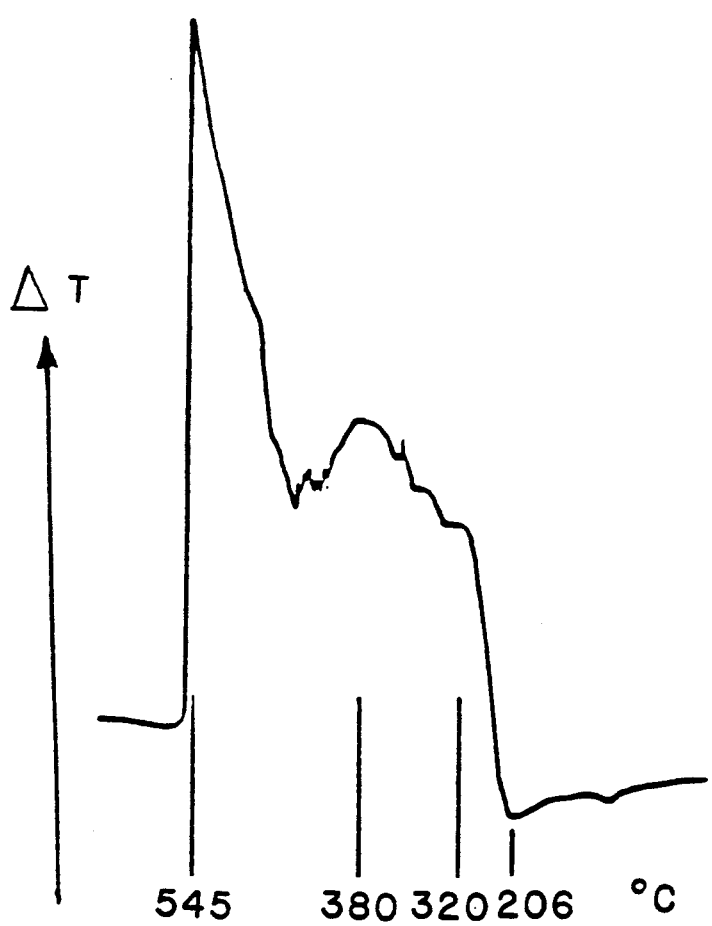
FIG. 3 is the thermal differential analysis for example 10.
Figure 4:
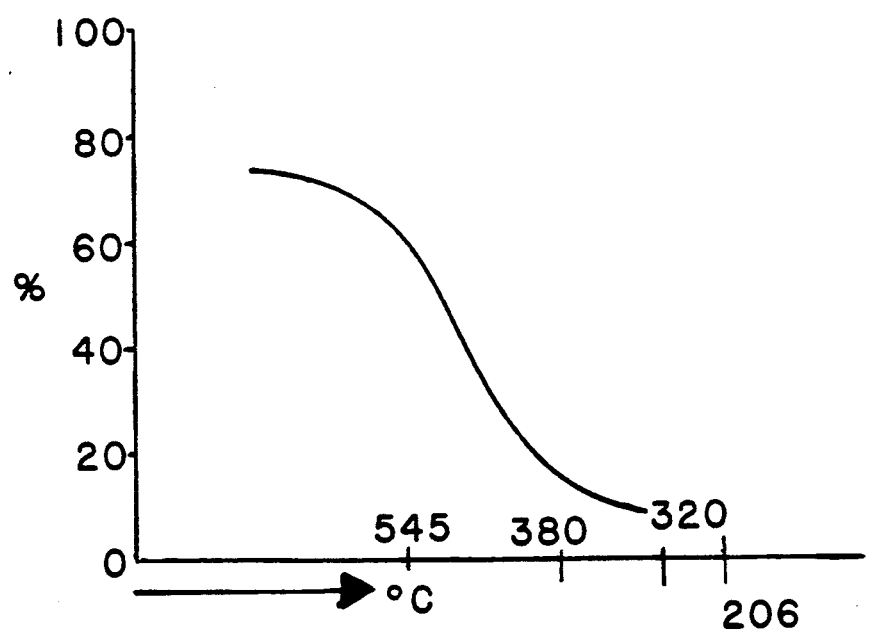
FIG. 4 is the thermal gravimetric analysis for example 10.

See FIG. 3 for thermal differential analysis and FIG. 4 for thermal gravimetric analysis for example 10.

EXAMPLE 11: PRODUCTION OF Al-Mg-HYDROXY BEHENATE
$Al_5Mg_{10}(OH)_{31}(C_{21}H_{43}COO)_4$ 528.6 g sodium behenate (from Example 5) was suspended by stirring in 4758 g water and was added to 2000 g Al-Mg-hydroxy sulfate suspension produced as in Example 1. The suspension was heated to 60.C for one hour to complete the reaction, was permitted to cool and then the insoluble Al-Mg-hydroxy behenate was filtered off. The filtrate was rinsed with water until no further sulfate could be detected. The filter cake was then dried at 105.C in a drying cabinet until a constant weight was attained.

Yield: 767 g (95% theoretical).

Description: white, odorless, crystalline powder.

Analysis: 5.8% Al in dry state (theory: 6.0%); 10.5% Mg in dry state (theory: 10.7%); 46.2% C in dry state (theory: 46.7%).

X-ray Powder Pattern (Apparatus: Philipps Automated X-Ray Powder Diffractometer, System APD 15) for Example 11

| Peak No. | 2 - theta | d (pm) | $I/I_o$ |
|---|---|---|---|
| 1 | 19.584 | 4 52.90 | 67 |
|   | 21.049 | 4 21.69 | 82 |
|   | 21.260 | 4 17.56 | 100 |
| 2 | 31.851 | 2 80.72 | 43 |
| 3 | 34.074 | 2 62.89 | 46 |
|   | 34.630 | 2 58.80 | 61 |
|   | 34.857 | 2 57.17 | 73 |
|   | 35.176 | 2 54.90 | 54 |
|   | 35.686 | 2 51.38 | 52 |
| 4 | 41.4 | 2 17. |  |
| 5 | 42.5 | 2 13. |  |
| 6 | 48.3 | 1 89. |  |
| 7 | 60.705 | 1 52.43 | 43 |
|   | 61.982 | 1 49.59 | 28 |

EXAMPLE 12: PRODUCTION OF Al-Mg-HYDROXY STEARATE
$Al_3Mg_{13}(OH)_{31}(C_{17}H_{35}COO)_4$

In an open basin, 578.2 g aluminum hydroxide paste containing 12.73% $Al_2O_3$ was diluted with 3151.4 g water and then 796 g aluminum sulfate solution containing 4.22% Al and 21.62% $SO_4$ was stirred in. The suspension was allowed to stand overnight to permit any $CO_2$ gas to escape and then 474 g MgO (commercially available) containing 99% MgO was added under stirring. This caused slight heating.

Analysis of the suspension: 1.40% Al, 5.60% Mg, 3.46% $SO_4$.

Under stirring, 969 g sodium stearate suspended in 7000 g water was added to 4469 g of the above suspension. The suspension was heated to 60° C. for one hour, was permitted to cool and then the insoluble Al-Mg-hydroxy stearate was filtered off. The filtrate was rinsed with water until no further sulfate could be detected. The filter cake was again suspended in 10 kg water and was spray-dried. The entrance temperature was 270° C. and the exit temperature was 100° C.

Yield: 1606 g (97% theoretical).

Description: white, odorless, crystalline powder.

Analysis: 3.7% Al in dry state (theory: 3.9 %); 15.3%Mg in dry state (theory: 15.4 %); 40.8%C in dry state (theory: 41.5 %).

EXAMPLE 13: PRODUCTION OF Al-Mg-HYDROXY STEARATE

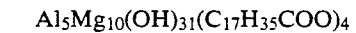

$Al_5Mg_{10}(OH)_{31}(C_{17}H_{35}COO)_4$

In an open basin, 1581 g aluminum hydroxide paste containing 12.3%$Al_2O_3$ was diluted with 3000 g water and then 975 g aluminum sulfate solution containing 4.21% Al and 21.54% $SO_4$ was stirred in. The suspension was allowed to stand overnight to permit any $CO_2$ to escape and then 446 MgO (99% purity) was added under stirring. This caused slight heating.

Analysis of the suspension: 2.41% Al, 4.40% Mg, 3.45% $SO_4$.

While stirring, 983 g sodium stearate suspended in 7000 g water were added to 4470 g of the above suspension. The suspension was heated to 60° C. for one hour, was permitted to cool and then the insoluble Al-Mg-hydroxy stearate was filtered off. The filtrate was rinsed with water until no further sulfate could be detected. The filter cake wa again suspended in 10 kg water and was spray-dried. The entrance temperature used was 275° C. and the exit temperature was 100° C.

Yield: 1556 g (95% theoretical).

Description: white, odorless, crystalline powder.

Analysis: 6.5%Al in dry state (theory: 6.6 %); 11.7% Mg in dry state (theory: 11.9 %); 42.0% C in dry state (theory: 42.4%).

Density: 1.19 g/ml

EXAMPLE 14: PRODUCTION OF Al-Mg-HYDROXY STEARATE
$Al_7Mg_7(OH)_{31}(C_{17}H_{35}COO)_4$

In an open basin, 2086 g aluminum hydroxide paste containing 12.73%$Al_2O_3$ was diluted with 1825 g water and then 824 g aluminum sulfate solution containing 4.22% Al and 21.62% $SO_4$ was stirred in. The suspension was allowed to stand overnight to permit any $CO_2$ to escape and then 264 MgO containing 99% MgO was added with stirring. This caused slight heating.

Analysis of the suspension: 3.4%Al, 3.2%Mg, 3.7 % $SO_4$.

With stirring, 1054 g sodium stearate suspended in 7000 g water was added to 4469 g of the above suspension. The suspension was heated to 60° C. for one hour, was permitted to cool and then the insoluble Al-Mg-hydroxy stearate was filtered off. The filtrate was rinsed with water until no further sulfate could be detected. The filter cake was again suspended in 10 kg water and was spray-dried. The entrance temperature was 270° C. and the exit temperature was 100° C.

Yield: 1668 g (96% theoretical).
Description: white, odorless, crystalline powder.
Analysis: 9.2% Al in dry state (theory: 9.3%); 8.1% Mg in dry state (theory: 8.4%); 41.9% C in dry state (theory: 42.3%).

EXAMPLE 15: PRODUCTION OF Al-Mg-HYDROXY STEARATE $Al_9Mg_4(OH)_{31}(C_{17}H_{35}COO)_4$

In an open basin, 2881 g aluminum hydroxide paste containing 12.73% $Al_2O_3$ was diluted with 1126 g water and then 839 g aluminum sulfate solution containing and 4.22% Al and 21.62% $SO_4$ was stirred in. The suspension was allowed to stand overnight to permit any $CO_2$ to escape and then 154 MgO (99% purity) was added with stirring. This caused slight heating.

Analysis of the suspension: 4.32% Al, 4.87% Mg, 3.85% $SO_4$.

Under stirring 1,098 g sodium stearate suspended in 7000 g water was added to 4469 g of the above suspension. The suspension was heated to 60° C. for one hour, was permitted to cool and then the insoluble Al-Mg-hydroxy stearate was filtered off. The filtrate was rinsed with water until no further sulfate could be detected. The filter cake was again suspended in 10 kg water and was spray-dried. The entrance temperature was 270° C. and the exit temperature was 100° C.

Yield: 1685 g (94% theoretical).
Description: white, odorless, crystalline powder.
Analysis: 12.0% Al in dry state (theory: 12.1%); 4.7% Mg in dry state (theory: 4.9%); 42.4% C in dry state (theory: 42.7%).

EXAMPLE 16: Production of Al-Mg-HYDROXY STEARATE $Al_5Mg_{10}(OH)_{31}(C_{17}H_{35}COO)_4$ In a stirring basin, 11.1 kg aluminum hydroxide paste containing 12.73% $Al_2O_3$ was diluted with 30 kg water and then 6.8 kg aluminum sulfate solution containing 4.2% Al and 21.5% $SO_4$ was stirred in. Stirring continued for three hours and then 3.1 kg MgO containing 99% MgO were added. This caused slight heating. After 3 further hours of stirring, 7.2 kg sodium stearate and 49 kg water were added. Stirring continued and for another two hours and then the suspension was treated with high shear forces to obtain a homogeneous paste. After further stirring (about one hour), the insoluble Al-Mg-hydroxy stearate was filtered using a filter press. The filtrate was rinsed with water until no sulfate could be detected. The filter cake was suspended in 70 kg water and spray-dried. The entrance temperature was 280° C. and the exit temperature was 90° C.

Yield: 10.5 kg (92% theoretical).
Description: white, odorless, crystalline powder.
Analysis: 6.5% Al in dry state (theory: 6.6%); 11.8% Mg in dry state (theory: 11.9%); 42.1% C in dry state (theory: 42.4%).

EXAMPLE 17: PRODUCTION OF Al-Mg-HYDROXY PALMITATE STEARATE $Al_5Mg_{10}(OH)_{31}(C_{15}H_{31}COO)(C_{17}H_{35}COO)_3$ 101 g sodium palmitate (from Example 4) and 335 g sodium stearate were suspended by stirring in 3930 g water and were added to 2000 g Al-Mg-hydroxy sulfate suspension produced as in Example 1. The suspension was homogenized in a "Turrax" stirrer and was stirred for three hours at room temperature. Then the suspension was filtered and freed of sulfates by rinsing with distilled water. The filter cake was dried at 95° C. in a drying cabinet until a constant weight was attained.

Yield: 693 g (95% theoretical).
Description: white, odorless, crystalline powder.
Analysis: 6.6% Al in dry state (theory: 6.7%); 11.5% Mg in dry state (theory: 12.0%); 41.4% C in dry state (theory: 41.8 %).

This application is related to subject matter disclosed in our application No. P 37 31 919.1-42 filed Sept. 23, 1987 in the Patent Office of the Federal Republic of Germany, the entire specification of which is incorporated herein by reference.

From the foregoing detailed description, it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

What is claimed is:

1. An aluminum magnesium hydroxy compound which is an anion-substituted magaldrate and of the formula $$Al_xMg_y(OH)_{35-z}R_z \cdot nH_2O$$

wherein R represents an anion selected from the group consisting of monocarboxylic acid anions having from 2 to 22 carbon atoms, and mixtures thereof, and n, x, y and z are defined by:

$0 \leq n \leq 10$ $3 \leq x \leq 9$ $4 \leq y \leq 13$ $3 \leq z \leq 5$ and $3x + 2y = 35$.

2. A compound as defined in claim 1, wherein x=5, y=10 and z=4.

3. A compound as defined in claim 1, wherein said at least one carboxylic acid anion is a mixture of aliphatic monocarboxylic acid anions having from 16 to 18 carbon atoms.

4. An aluminum magnesium hydroxy compound which is an anion-substituted magaldrate and of the formula $$Al_5Mg_{10}(OH)_{31}R_4 \cdot nH_2O$$

wherein R represents an anion selected from the group consisting of monocarboxylic acid anions having from 16 to 18 carbon atoms, and mixtures thereof, and $0 \leq n \leq 10$.

5. A process of producing an aluminum magnesium hydroxy compound, comprising the steps of:
mixing an aqueous suspension of a compound of magaldrate structure and the formula $Al_xMg_y(OH)_{35-z}(SO_4)_{z/2} \cdot nH_2O$, wherein n, x, y and z are defined by $0 \leq n \leq 10$
$3 \leq x \leq 9$ -continued $$4 \leq y \leq 13$$
$$3 \leq z \leq 5 \text{ and } 3x + 2y = 35.$$

at a temperature of from about 20° C. to about 100° C. with one of a solid alkali salt of at least one monocarboxylic acid or an alkali salt of at least one monocarboxylic acid suspended in water, wherein said at least one monocarboxylic acid has 2 to 22 carbon atoms, to produce a reaction mixture; and recovering a solid component from said reaction mixture.

6. A process as defined in claim 5, wherein said temperature is from about 20° C. to about 60° C.

7. A process as defined in claim 5, comprising the further step of subjecting said reaction mixture to shear forces.

8. A process as defined in claim 5, wherein said step of recovering the solid component from said reaction mixture comprises filtration to produce a filter cake.

9. A process as defined in claim 8, comprising the further step of rinsing said filter cake until it is free of sulfate ions, to produce a sulfate-free filter cake.

10. A process as defined in claim 9, comprising the further step of drying said filter cake at a drying temperature from about 60° C. to about 130° C.

11. A process as defined in claim 10, wherein said drying temperature is in a range from about 80° C. to about 110° C.

12. A process as defined in claim 9, comprising the further steps of:

resuspending said sulfate-free filter cake in water to produce a resuspension;

spray-drying said resuspension at an entrance temperature $T_E$ of from about 250° C. to about 350° C. and at an exit temperature $T_A$ of from about 80° C. to about 130° C.

13. A process as defined in claim 12, wherein $T_E$ is from about 270° C. to about 300° C.

14. A process as defined in claim 12, wherein $T_A$ is from about 90° C. to about 110° C.

* * * * *